US00PP25063P3

(12) United States Plant Patent
Austin

(10) Patent No.: US PP25,063 P3
(45) Date of Patent: Nov. 18, 2014

(54) ***ROSA HYBRIDA* SHRUB NAMED 'AUSNOBLE'**

(50) Latin Name: *Rosa hybrida*
Varietal Denomination: AUSnoble

(71) Applicant: David Austin Roses Ltd., Wolverhampton (GB)

(72) Inventor: David J. C. Austin, Wolverhampton (GB)

(73) Assignee: David Austin Roses Ltd., Albrighton, Wolverhampton (GB)

( * ) Notice: Subject to any disclaimer, the term of this patent is extended or adjusted under 35 U.S.C. 154(b) by 40 days.

(21) Appl. No.: 13/986,073

(22) Filed: Mar. 28, 2013

(65) Prior Publication Data

US 2014/0075605 P1 Mar. 13, 2014

(51) Int. Cl.
*A01H 5/00* (2006.01)

(52) U.S. Cl.
USPC ..... Plt./103

(58) Field of Classification Search
USPC ..... Plt./103
See application file for complete search history.

*Primary Examiner* — Kent L Bell
(74) *Attorney, Agent, or Firm* — KPPB LLP

(57) ABSTRACT

A variety of rose plant of the shrub class, named 'AUSnoble', suitable for repeat flowering production having a vigorous upright growth that is very healthy with light green foliage that is almost thornless, and that produces beautifully rounded flowers with neatly placed petals making a perfect rosette, with buds that are lightly tinged yellow, but with flowers that open to become pure white, and that produce a light apple fragrance.

1 Drawing Sheet

Classification: The present invention relates to a new *Rosa hybrida* shrub.

Variety denomination: The new plant has the varietal denomination 'AUSnoble'.

CROSS-REFERENCE TO RELATED APPLICATIONS

The current application claims priority to a European Plant Breeder's Rights Application No. 2012/1943, filed Sep. 12, 2012, the disclosure of which is incorporated herein by reference.

ORIGIN OF INVENTION

This invention relates to a new and distinct variety of shrub rose plant named 'AUSnoble', which was originated by crossing two unnamed, unpatented varieties of *Rosa hybrida.*

BACKGROUND OF THE INVENTION

The primary objective of this breeding was to grow a rose with a vigorous upright growth that is very healthy with light green foliage that is almost thornless, and that produces beautifully rounded flowers with neatly placed petals making a perfect rosette, with buds that are lightly tinged yellow, but with flowers that open to become pure white, and that produce a light apple fragrance.

SUMMARY OF THE INVENTION

Among the features which distinguish the new variety from other presently available and commercial rose cultivars known to the inventor is the following combination of characteristics: pure white rosette shaped blooms, a light apple fragrance, and light green musk rose foliage with almost thornless stems.

Asexual reproduction of the new variety by budding as performed in greenhouses at Bowling Green Lane in Albrighton, Britain shows that the foregoing and other distinguishing characteristics come true to form and are established and transmitted through succeeding asexual propagations. 'AUSnoble' may be asexually propagated by budding. The budding successfully occurred on the plant/rootstock *Rosa* cv. 'Dr. Huey' in the United States, and on the plant/rootstock *Rosa dumetorum* cv. 'Laxa' in the United Kingdom.

COMPARISON WITH PARENTS

The new rose may be distinguished from its seed parent, by the following combination of characteristics: whereas the seed parent has smaller pink flowers and is less disease resistant, 'AUSnoble' bears white flowers that are very healthy. The new variety is classified as a *hybrida* rose.

The new variety may be distinguished from its pollen parent, by the following combination of characteristics: whereas the pollen parent bears pink semi-double flowers, 'AUSnoble' bears double blooms of pure white.

COMPARISON WITH THE CLOSEST COMMERCIALLY AVAILABLE CULTIVAR

The closest commercially available cultivars to the new variety are the 'AUSprior' (U.S. Plant Pat. No. 19,465) and 'AUSrelate' (U.S. Plant Pat. No. 18,702). The new rose may be distinguished from the 'AUSprior' variety by the following combination of characteristics: 'AUSprior' has a more arching growth habit and is taller (making a climber of up to 2.4 m), whereas 'AUSnoble' makes a more upright shrub reaching 1.25 m. In addition, the blooms of 'AUSprior' are more cupped than those of 'AUSnoble', which flatten to form rosettes. Likewise, the new rose may be distinguished from the 'AUSrelate' variety by the following combination of characteristics: 'AUSrelate' bears blooms of an apricot color with a fragrance that has strong notes of clove, whereas 'AUSnoble' has pure white blooms with an apple fragrance.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

The following description is of 1 year-old rose plants of the new variety grown outdoors in Albrighton, Britain in the month of July. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

*Size*.—About 2 cm long and 2.3 cm in diameter when the petals start to unfurl.

*Form*.—The bud form is globular.

*Color*.—When sepals first divide, the bud color is Yellow-green (RHS 1D) and Red-purple (RHS 58A). When half blown, the upper sides of the petals are RHS 155C, and the lower sides of the petals are RHS 155C.

*Sepals*.—Color: Upper Surface: (RHS 147C). Lower Surface: (RHS 144A). Length: 2.3 cm. Width: 10 mm. Shape: Lanceolate. Surface texture: Upper Surface: Downy. Lower Surface: Smooth. Number: There are three lightly appendaged sepals. There are 2 unappendaged sepals with hairy edges.

*Receptacles*.—Color: Green (RHS 143A). Shape: Funnel. Size: broad, about 0.8 cm×1 cm. Surface: Smooth.

*Peduncle*.—Length: medium, averaging about 7 cm. Surface: rough. Color: Medium green with some reddish tints. Strength: Strong.

Blooms:

*Size*.—Large, average open diameter is about 9 cm.

*Borne*.—Singly in clusters of 1-4 blooms having rounded shape.

*Stems*.—Strength: Strong, average length is about 8 cm. Diameter: 5 mm.

*Form*.—When first open, bloom is cupped. Permanence of bloom: flattens.

*Petalage*.—Number of petals under normal conditions: 110.

*Color*.—The upper sides of the petals are White (RHS 155C). The reverse sides of the petals are White (155C). The base of the petals is (RHS 155C).

*Variegations*.—N/A.

*Discoloration*.—The general tonality at the end of the first day is (RHS 155C) and at the end of the third day is (RHS 155C).

*Fragrance*.—Slight. Character of fragrance: Light apple.

Petals:

*Texture*.—Smooth.

*Size*.—Width: 2.4 cm. Length: 4 cm.

*Surface*.—Smooth.

*Shape*.—Obovate.

*Margin*.—Entire with some petals notched, weak undulation.

*Apex shape*.—Rounded.

*Base shape*.—Obtuse.

*Form*.—Slightly incurved.

*Arrangement*.—Imbricated.

*Petaloids*.—Number: 4-6. Color: Petal: RHS 155C; Anther: RHS 4D; Filament: RHS 4D. Length: Petal: 10-25 mm. Anther: 2 mm. Filament: 4 mm.

*Persistence*.—Petals hang on and dry.

*Lastingness*.—On the plant: long, about 8 days. As a cut flower: not tested.

Reproductive parts:

*Stamens*.—Number: 45. Length: 6 mm.

*Anthers*.—Length: 2 mm. Color: RHS 15A. Arrangement: Regular around styles.

*Filaments*.—Color: Yellow-orange (RHS 14C). Length: 4 mm.

*Pollen*.—Color: Yellow-orange (RHS 15A).

*Pistils*.—Number: Average. Length: 4.8 mm and 7.8 mm (two distinctive lengths are observed).

*Styles*.—Color: (RHS 154D). Length: 4 mm & 7 mm.

*Stigmas*.—Color: (RHS 39B). Length: 0.8 mm.

*Hips*.—None Observed.

PLANT CHARACTERISTICS

Plant form: Shrub.

Plant growth: Vigorous, upright, bushy.

Age to maturity: Two years.

Mature plant: Height: 120 cm. Width: 90 cm.

Rootstock: *Rosa* 'Dr. Huey' for U.S. and *Rosa dumetorum* 'Laxa' for observed plants in the U.K.

Foliage:

*Number*.—Leaflets on normal mid-stem leaves is: 3 or 5 (including terminal leaflet).

*Size*.—Medium, about 14 cm long×12 cm wide.

*Quantity*.—Abundant. Number of leaves per flowering stem is: 8.

*Color*.—New foliage: Upper side: Yellow-Green Group (RHS 146B). Lower side: Yellow-Green RHS (146C). Old foliage: Upper side: Yellow-Green Group (RHS 147A). Lower side: Yellow-Green RHS (146B).

Leaflets:

*Size*.—About 6 cm long×4.5 cm wide.

*Shape*.—Broadly Oval.

*Base shape*.—Rounded.

*Apex shape*.—Acuminate.

*Texture*.—Leathery.

*Edge*.—Serrated.

*Serrations*.—Single.

*Petiole*.—Color: Green (RHS 143A). Length: 4.5 cm. Width: 18 mm. Surface Texture: smooth.

*Petiole rachis*.—Color: Greyed-orange (RHS 174A). Underside: smooth.

*Stipules*.—Length: 2.6 cm, smooth with a glandular margin. Color: Yellow-green (146C).

*Auricle*.—Shape: Sword-shaped. Length: 6 mm. Width: 2 mm. Color: Yellow-Green (RHS 146C).

*Vein color*.—As leaf color.

*Venation pattern*.—Reticulate.

Wood:

*New wood*.—Color: Violet-red (RHS 178B). Bark: Smooth.

*Old wood*.—Color: Light-Green (RHS 146B). Bark: Smooth with some rough patches.

Stems:

*Mature stem*.—Length: 60 cm. Diameter: 8 mm.

*Internode distance*.—8 cm. The above measurements are all variable, depending on growing conditions in a season.

*Stem pubescence present*.—No.

Prickles:

*Quantity*.—On main canes from base: few. Number per stem length: 3 per 10 cm. On laterals from main canes: few. Number per stem length: 2 per 10 cm.

*Form*.—Deep concave.

*Length*.—6 mm.

*Color when young*.—Greyed-red (RHS 182B).

*Color when mature*.—Greyed-orange (RHS 177D).

Small prickles:

*Quantity*.—Main stalk: None.

Disease resistance:

*Mildew*.—Resistant.

*Blackspot*.—Resistant.

*Rust*.—Resistant.

Pest resistance: Not tested.

Winter hardiness: Not tested.

Growing conditions: Normal.

What is claimed is:

1. A new and distinct variety of rose plant of the shrub class suitable for repeat flower production, substantially as herein shown and described.

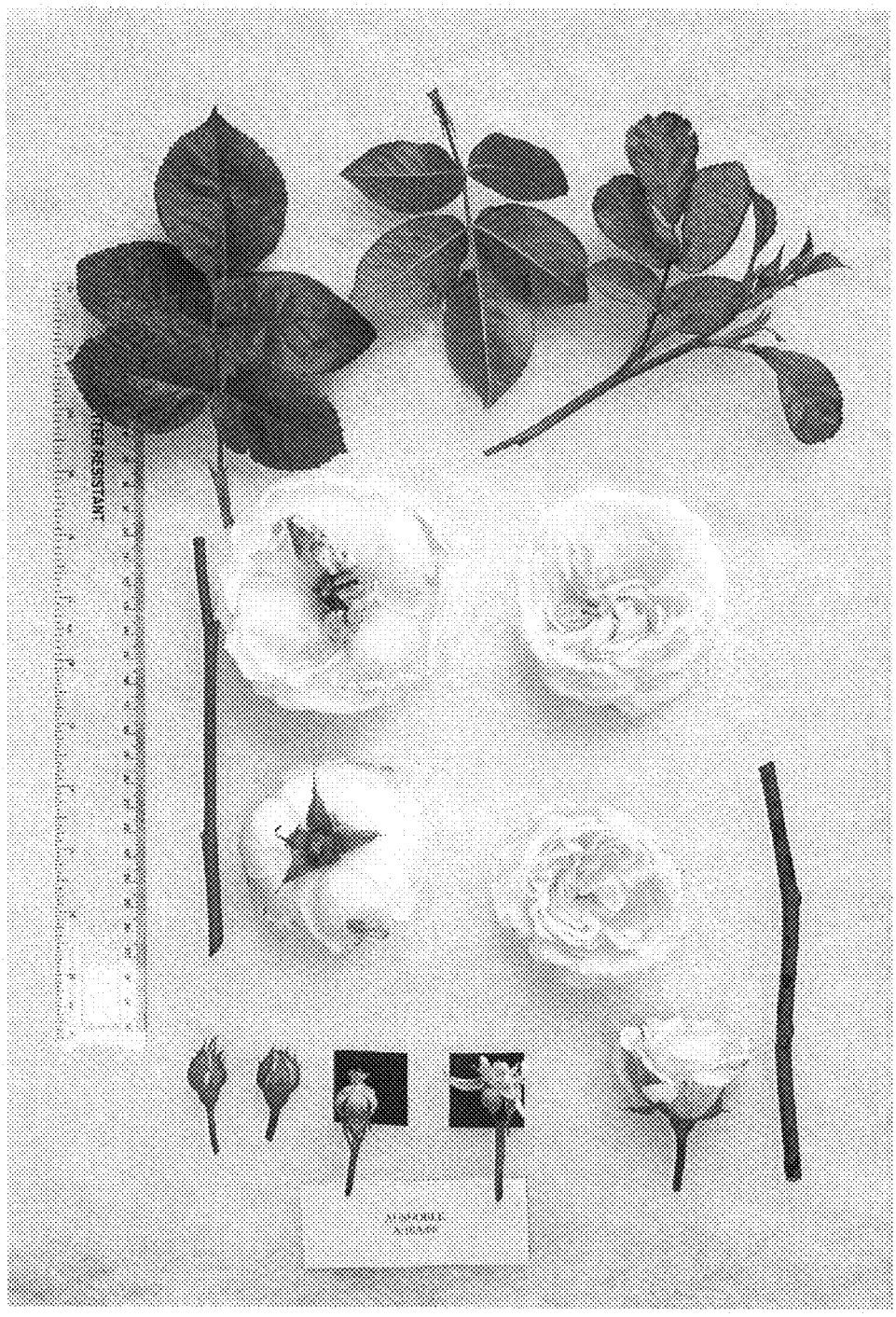

* * * * *